United States Patent [19]

Poncy et al.

[11] 4,159,069
[45] Jun. 26, 1979

[54] SURGICAL GLOVE PACKAGE

[76] Inventors: Mark P. Poncy; George W. Poncy; Richard P. Poncy, all of 3670 E. Industrial Way, Riviera Beach, Fla. 33404

[21] Appl. No.: 882,591

[22] Filed: Mar. 2, 1978

Related U.S. Application Data

[63] Continuation-in-part of Ser. No. 819,842, Jul. 28, 1977.

[51] Int. Cl.² .............................................. A47J 51/06
[52] U.S. Cl. ...................................... 223/111; 206/278
[58] Field of Search ................ 223/111, 112; 206/278, 206/438, 439, 440; 2/16, 160, 161 R

[56] References Cited

U.S. PATENT DOCUMENTS

| 882,312 | 3/1908 | Hoefftcke | 223/111 |
| 1,996,377 | 4/1935 | Hinchen | 223/111 |
| 4,002,276 | 1/1977 | Poncy et al. | 223/111 |
| 4,069,913 | 1/1978 | Harrigan | 206/278 |

Primary Examiner—Henry Jaudon
Attorney, Agent, or Firm—Lane, Aitken & Ziems

[57] ABSTRACT

In a surgical glove package, the cuff of the elastomeric glove is stretched around a D-shaped packaging ring so that the glove cuff extends radially back towards the center of the ring. Also extending around the ring is a flexible, transparent liner covering the outside surface of the glove and between the glove cuff and the ring so that the cuff holds the liner securely to the ring. The glove is oriented with respect to the ring so that the thumb is suspended directly below the junction of the straight portion of the D-shaped ring and the curved portion and so that the palm portion of the glove faces in the direction of the straight portion of the D-shaped ring. The glove is donned and removed from the ring by using the liner to manipulate the glove package. The glove package can also be used in connection with an inflating apparatus which inflates the glove prior to inserting a hand into the inflated glove.

10 Claims, 5 Drawing Figures

SURGICAL GLOVE PACKAGE

CROSS-REFERENCE TO RELATED APPLICATIONS

This application is a continuation-in-part of application Ser. No. 819,842 filed July 28, 1977, entitled "SURGICAL GLOVE PACKAGE AND DONNING SYSTEM" by the inventor of the application. Application Ser. No. 819,842 is related to application Ser. No. 797,384 entitled "SURGICAL GLOVE PACKAGE AND DONNING METHOD" filed May 16, 1977 by the inventor of this application. Application Ser. No. 797,384 is a continuation of application Ser. No. 618,336 filed Oct. 1, 1975 which is now abandoned. Application Ser. No. 618,336 is related to U.S. Pat. No. 4,002,276 entitled "SURGICAL GLOVE DONNING SYSTEM" issued Jan. 11, 1977 to the inventor of this application filed Aug. 1, 1975.

BACKGROUND OF THE INVENTION

A severe problem has existed in the use of surgical sterile gloves, particularly in operating rooms where procedures for maintaining sterility have to be strictly followed. Specifically, the problem is that the surgeon and other operating room personnel must don the sterile gloves without letting the outside surfaces of the gloves or their sterile gowns come into contacts with any non-sterile surface. This is a difficult procedure because, despite vigorous and prolonged scrubbing, the skin of the operating room personnel is not sterile and contact between the outer glove surfaces and the bare hand, wrist and forearm must be avoided. In addition, while the inside surfaces of the glove may be touched, the contact between the skin and the inside surface of the glove should be confined to the portion of the glove as far inward and away from the edge of the cuff as possible. The cuff portion of the glove when the glove has been donned fits over the sleeve of the gown, and, during operation, the gown cuff will often pull out of the glove cuff to some extent, in which case the gown cuff formerly covered by the glove cuff will be exposed. As a result, any contamination that may have been present on the inside of the glove cuff will have been transferred to the gown cuff now exposed and the exposed, contaminated surface may come into contact with body tissue within the surgical wound.

In the present operating room procedure in which several persons must be gloved, a circulating nurse is employed who is not sterile and who will not take part in the sterile procedures. This circulating nurse is charged with responsibility of opening all the sealed packages containing sterile items but which are presumed to be contaminated on the outside. These items include sterile gowns which will be worn by all attending personnel and sterile gloves. All the sealed packages are designed in such a way that the outer envelope of each package may be peeled open and spread in a flat position on the table in such a way that the inner surfaces of the envelope constitute a sterile field which the circulating nurse does not touch. In a sterile glove package, the outer envelope contains inner folded paper wrap, which in turn contains a pair of sterile gloves.

After the circulating nurse has opened the packages, containing the sterile materials, a second nurse referred to as a scrub nurse, who will later assist in handling sterile objects, is gowned with the assistance of the circulating nurse in such a way that the circulating nurse does not touch the outside of the sterile gown. The gown has long sleeves which are tapered to fit snugly around the wrists of the wearer. After being gowned, the scrub nurse proceeds with the self-donning of sterile gloves using either one of two alternative methods, one of which is referred to as the open method and the other is referred to as the closed method.

In the open method, the scrub nurse opens the inner folded wrapper containing the sterile gloves to expose the gloves lying side by side. The gloves are packaged with a considerable portion of the cuff turned over on itself. The scrub nurse grasps the right glove with her left hand near the folded edge of the cuff portion while maintaining the area of contact between her left hand and the glove as far away as possible from the edge of the cuff. The nurse then inserts her right hand into the glove attempting full entry of the fingers into the tightly fitting glove by tugging with her left hand on the folded over cuff portion. Care must be taken at this point to avoid premature snapping back or unfolding of the cuff portion. To avoid this occurrence, the thumb of the hand being gloved may be hooked into the folded over cuff portion until full entry is made into the finger portion. The folded cuff portion is then unfolded and allowed to snap back along the wrist portion of the hand over the cuff. In carrying out the unfolding of the cuff, care must be taken to avoid touching the outer glove surface and confining contact to the inner surface as far away as possible from the cuff edge. At the same time, care must be exercised to make sure that the left hand of the scrub nurse does not touch the sterile gown cuff. This step of unfolding the cuff of the first glove is an extremely critical point in the open method and it is believed by operating room personnel that contamination occurs more than fifty percent of the time during this step of the procedure. Once the right hand is gloved, the left glove is picked up with the gloved right hand by inserting the gloved hand into the folded cuff portion of the glove. Becaue the outside surface of the glove on the gloved hand is sterile, contact between the gloves' outer surfaces is permitted. The left glove is pulled on by the gloved hand exerting pressure inside of the folded cuff portion and the cuff is unfolded and allowed to snap back along the wrist portion and over the left gown cuff. At this point, care must again be taken to avoid premature unrolling of the glove cuff to avoid contamination of the edge of the cuff that would result from contact with the skin at the wrist portion.

The high incidence of glove contamination which occurs in the open method has led to the adoption in some operating room of the closed method of donning the gloves. The closed method, while lessening the chance of contamination of the gloves, imposes a difficult and almost acrobatic technique upon the scrub nurse who must don the gloves without assistance. In the closed procedure, as in the open method, the scrub nurse is already gowned with the gown having full length tapered sleeves over which the cuff portions of the gloves will be snapped. In this method, instead of grasping the right glove with the bare fingers, the nurse grasps the glove through the gown sleeves. To carry out this technique, the nurse does not put her hands through the sleeve openings, but lets the gown sleeves cover her hands. The scrub nurse grasps the right glove in her left hand through the sleeve and positions the glove over her right wrist with the glove fingers pointing up the arm. Then, still working with her left hand through the left gown sleeve and with her right hand still inside the right sleeve, the nurse inserts the right sleeve cuff into the right glove cuff and snaps the right glove cuff over the right sleeve cuff. Then the nurse grasps the right sleeve cuff, now covered by the glove cuff, with the left hand still working through the left sleeve and pulls the right glove onto the right hand until as much entry into the fingers as can be achieved is effected. The process is then duplicated for the left hand except that the nurse does not work on the left glove through the right sleeve. The nurse, however, must maintain the ungloved left hand inside the sleeve until the left glove is snapped around the left sleeve cuff. The closed procedure is very difficult and requires a lot of practice to develop any proficiency in the procedure.

The above described procedures are concerned with the self-donning of the gloves the the scrub nurse and must be undertaken in order to provide a sterile nurse who can assist the others in the operating room in donning their gloves.

In assisting the donning of a second person, the scrub nurse, who is already gloved, picks up a sterile glove and places the fingers of both hands inside the folded over cuff portion exerting outward pressure in an attempt to stretch open the opening presented to the person to be donned. The donner, often the surgeon, then vigorously thrusts his hand up and into the glove. The nurse must maintain a steady force against this thrust by the surgeon who is attempting an initial thrust to gain access to the fingers of the glove. Almost in the same motion, the nurse thrusts forward and, by letting go of the glove cuff at the right moment, attempts to cause the cuff to snap over the surgeon's gown cuff without any rollover of the cuff edge.

Because of the difficulty in fully inserting hands into the gloves, the inner surface of the gloves must be heavily powdered to lubricate the glove surface relative to the hands. This powder in operation normally results in powder getting on the external surfaces of the glove. As a result, the surgeon must use sterile wipes to cleanse the glove surfaces of powder because the presence of powder particles in a surgical wound would aggravate the internal organs and tissue and would adversely affect healing following surgery.

While sterile gloves are necessary in operating rooms, a greater number of sterile gloves are used in procedures outside of operating rooms. Usually outside of the operating rooms, the person donning the glove must don the gloves without assistance. In many of these instances, a gown is not used, so the person donning the glove has no alternative but to use the open method of donning with its attendant greater risks of accidental contamination. In these instances, the contamination often occurs when attempts are made to prevent the cuff from rolling or in straightening out a cuff that has rolled over.

While the procedures an requisites, described above, necessary to avoid contact with unsterile surfaces are strictly required, in actual practice, accidents of contamination have been commonplace.

The invention described in application Ser. No. 819,842 provides a sterile glove package which permits the sterile glove to be donned quickly, easily, without assistance while maintaining the sterility of the glove surface and without any powder appearing on the outside of the glove. The glove is packaged with a ring and a flexible liner covering the outside surface of the glove. The liner extends through the ring with the edge of the liner folded over the outside of the ring. The glove extends through the middle of the ring inside of the liner and the cuff of the glove is stretched around the outside of the ring with the edge of the cuff extending back in toward the middle of the ring so that the cuff defines a round opening through which the material of the liner and the hand and the finger portion of the glove extend. The ring of the package thus holds the cuff of the gloves open for insertion of the hand into the glove.

With the above described package, the gloves can be donned very easily and with little danger of the outside glove surfaces coming into contact with the contaminated surface and also contact of the inside of the cuff of each glove and contaminated surfaces can be completely avoided except where the glove comes into contact with the wrist of the person wearing the glove beyond the end of the gown sleeve. The liner covering the outside surface of the glove provides a convenient microbial barrier through which the glove can be manipulated during the donning procedure to maintain the surface of the glove sterile. Moreover, because the liner covers the outside surface of the glove, the inside surface of the glove can be powdered with lubricating, moisture absorbing powder without any of the powder getting on the outside surface of the glove in contrast with present day packages in which powder is always all over the outside of the gloves as well as inside the gloves.

SUMMARY OF THE INVENTION

The present invetion is an improvement over the glove package described in the copending application Ser. No. 819,842 in that the packaging ring, around which the glove cuff is stretched, instead of being a circular ring, is D-shaped. The ring has a circular, arcuate segment of about 260 degrees and a linear segment subtending an arc of about 100 degrees. The glove is oriented with respect to the D-shaped ring so that the thumb is suspended directly below the junction between the linear segment and the arcuate segment and so that the palm portion of the glove faces in the general direction of the linear segment but suspended beneath it. The person donning the glove with this arrangement has an obvious point to grasp when picking up the ring thus obviating the need for the donner to find the orientation of the glove by visual inspection and rotating the package in order to line the glove up with his hand as is necessary with a completely circular ring. To identify the right glove as distinct from the left glove, the rings are color coded with red being selected for the right glove.

DESCRIPTION OF THE PREFERRED EMBODIMENT

Figure 1:
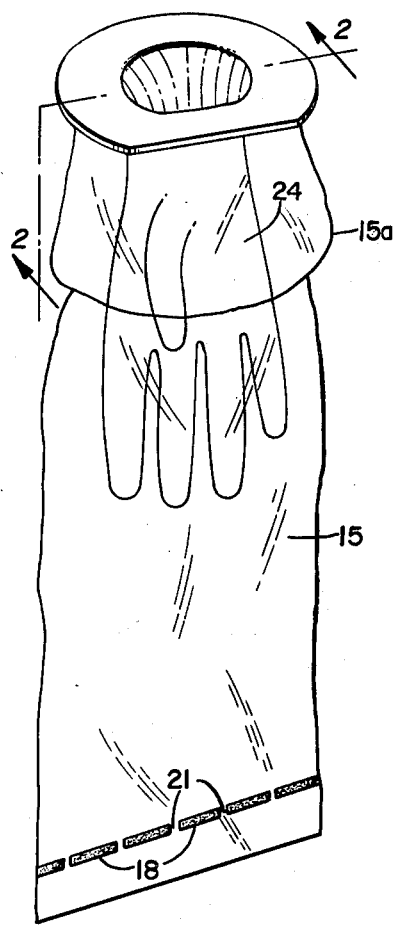
FIG. 1 is a perspective view of the glove package for the right hand.
Figure 2:
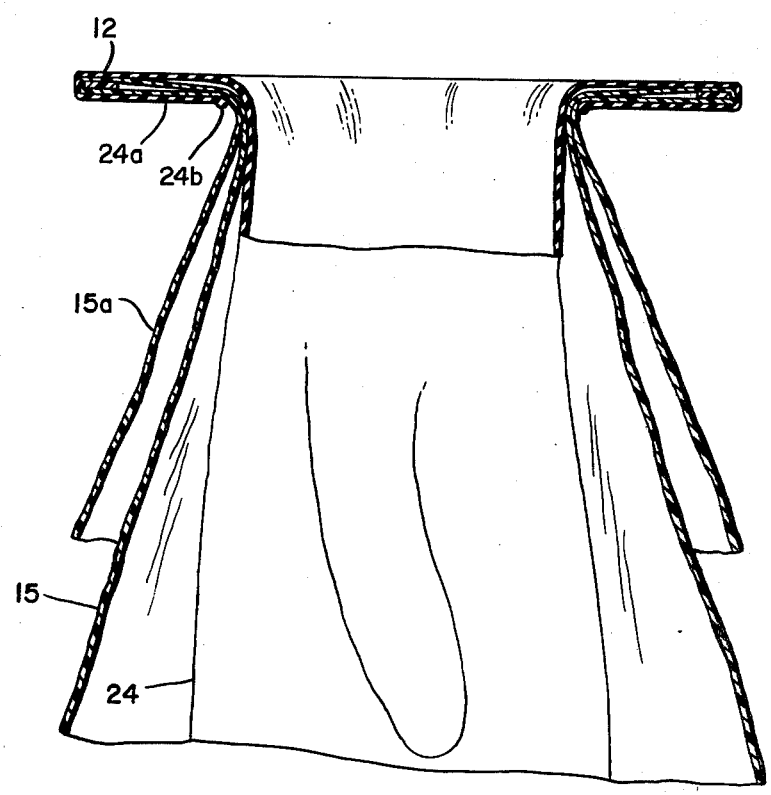
FIG. 2 is a sectional view taken along the line 2—2 of FIG. 1.
Figure 3:
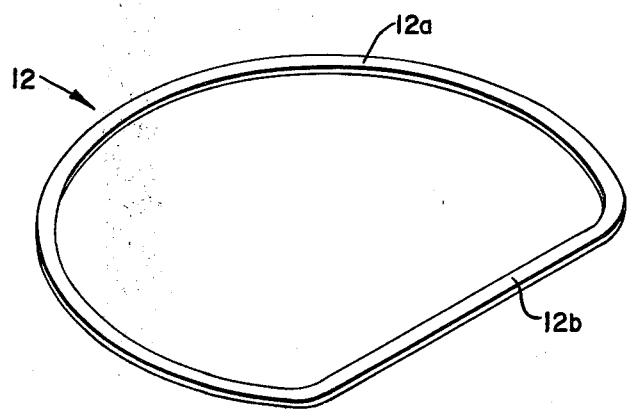
FIG. 3 is a perspective view of the D-shaped packaging ring of the invention.

As shown in FIGS. 1-3, the glove package of the present invention comprises a D-shaped packaging ring 12 which may be molded from a rigid plastic such as styrene or high density polyethelene.

The D-shaped ring 12 comprsies a circular arcuate portion 12a extending for about 260° and a linear portion 12b subtending what would be an arc of about 100° if the ring were a complete circle. The inner diameter of the ring in the circular portion is sized so that a human hand can be inserted through the ring in the normal folded position for donning a glove, that is with the fingers together and extended and the thenar portion of the palm folded under with the thumb also extended beneath the fingers. The outer diameter is sized so as not to stretch the cuff of the elastic glove so far as to deliteriously affect its elasticity. In the preferred embodiment, the circular portion of the ring has an outer diameter of 4¾ inches and an inner diameter of 4 9/16 inches. The inner diameter should be at least 4¼ inches to readily permit insertion of an adult human hand and the outer diameter should be no more than 5¼ inches to prevent over stretching of the glove cuff. In the preferred embodiment, the ring is 3/32 of an inch thick. The ring, instead of being made of a rigid plastic, may be made of paperboard, in which case the dimension of the ring in the axial direction should be made greater in order to provide sufficient strength to the ring.

A thin, transparent, flexible liner 15 in the form of a tube has one end extending up through the middle of the ring and turned down over the ring to form a skirt 15a hanging down from the ring. The other end of the tube forming the liner 15 is closed by seal 18 extending across the other end of the tubular liner. The seal 18 is formed in a manner to leave small openings 21 so as to communicate the interior of the liner with the exterior. The seal 18 thus makes the liner 15 into a bag. A glove 24 made of thin, elastomeric material has its palm and finger portions extending down through the middle of the ring 12 into the interior of the liner 15. The cuff portion 24a of the glove is mounted on the ring by being stretched over the ring with enough overlap to go entirely around the ring so that the cuff portion 24a, which is under elastic tension, extends radially back toward the center of the ring. The cuff edge 24b defines a hole through which the part of the liner 15 extending through the ring 12 as well as the skirt 15a is gathered. Because the elastomeric material of the glove cuff is stretched over the liner around the outside of the ring, it holds the liner securely mounted on the ring. The glove 24 is oriented with respect to the ring 12 so that the palm portion of the glove faces in a direction toward a plane parallel to the axis of the ring and containing the linear segment 12b. The closest part of the ring 12 to the thumb portion of the glove is the junction between the linear segment 12b and the arcuate circular portion 12a.

The ring 12 with its linear segment provides a reference for the manufacturer to easily mount the glove on the ring with the above described orientation. With the glove so oriented, the donner of the glove now has an obvious point to grasp when picking up the ring, thus eliminating the need for the donner to visually inspect the package to line the glove up with the hand to be inserted as is necessary with a circular ring. The linear portion, while reducing the size of the opening in the ring, does not effectively restrict the space for inserting a hand. The D-shaped ring is ideally shaped to insert a hand through in the normal closed position for donning a glove. The linear segment just restricts the space in an area which is not needed for the insertion of the hand.

The linear segment 12b is preferably made to subtend an arc of 100°. However, it may subtend larger angles up to 180° or smaller angles down to 45°. It should subtend an angle which is large enough so as to be readily distinguishable from the circular portion.

After the glove has been mounted on the ring and the lubricating powder is applied to the interior of the gloves, the powder will not get on the outside of the glove because of the liner 15. After the interior of the glove has been powdered, it is packaged with packaging materials (not shown) and sterilized in a conventional manner as by ethelene oxide gas.

The gloves may then be donned by the methods described in the copending application Ser. No. 819,842 which is incorporated by reference.

The package may be used with an inflating apparatus similar to that disclosed in Ser. No. 819,842. As described in that application, the package is held between the skirt 15a and the remaining portion of the liner 15 and the bottom or sealed end of the liner is pulled out to fully extend the liner. The package is then placed over the opening of the inflating apparatus as shown in FIG. 5.

Figure 4:
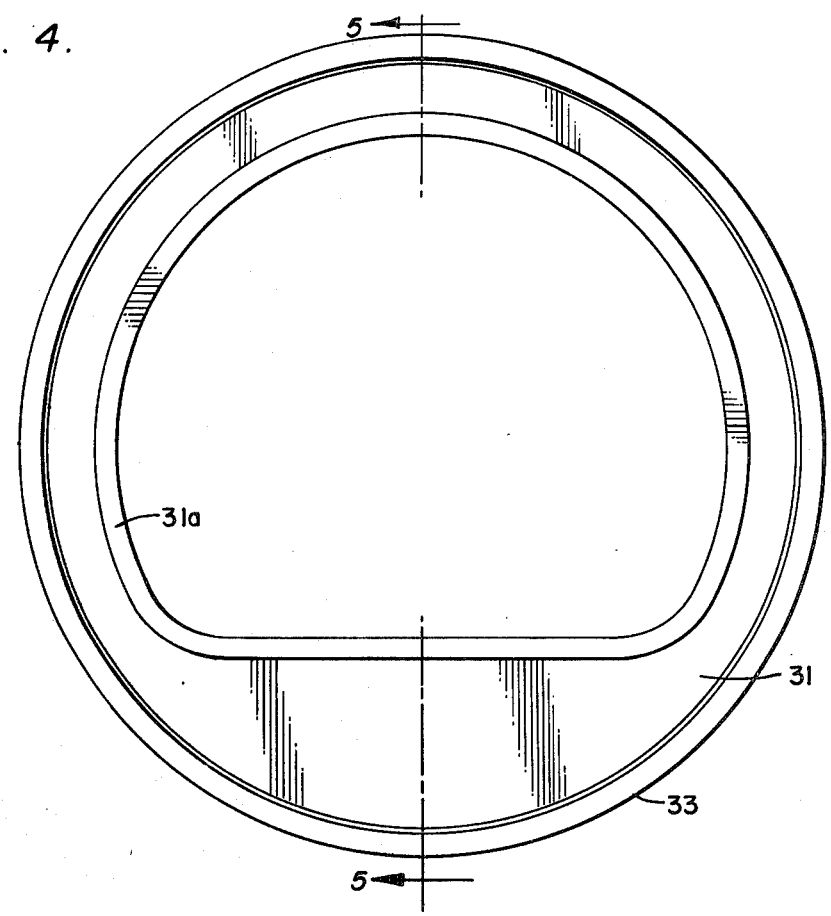
FIG. 4 is a top plan view of a glove inflating apparatus for inflating the glove of the package of FIGS. 1 and 2 to facilitate the donning of the glove.
Figure 5:
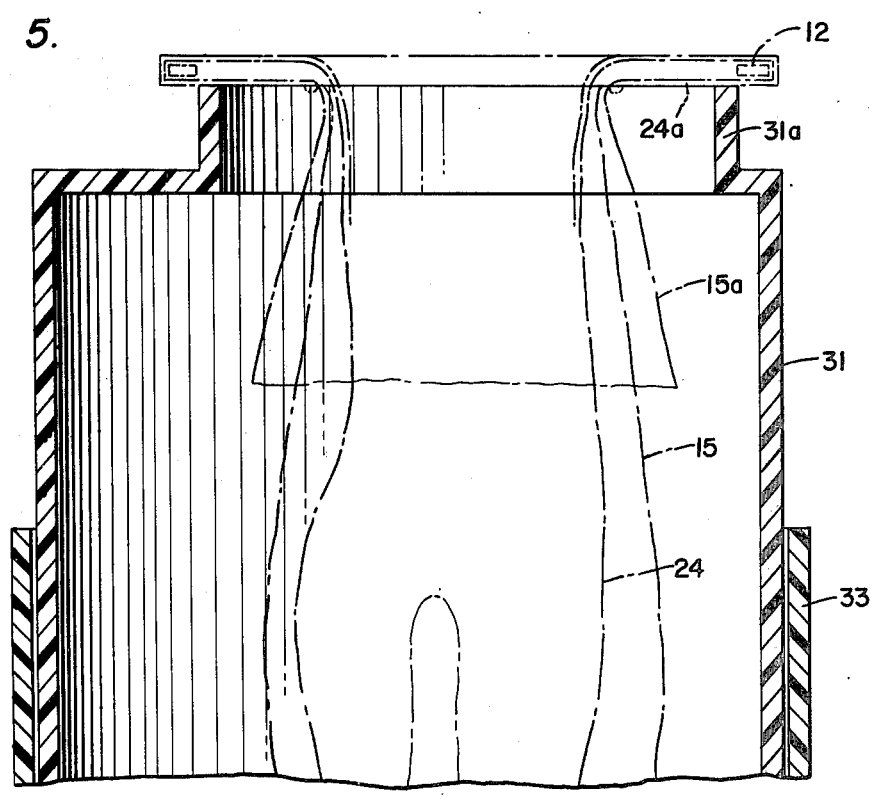
FIG. 5 is a sectional view taken along the line 5—5 of FIG. 4 and showing in phantom lines the glove package in place ready to be inflated.

The inflating apparatus as shown in FIGS. 4 and 5 is the same as that described in the copending application Ser. No. 819,842 except that it has been modified to accommodate the D-shaped packaging ring. The inflating apparatus comprises an inner cylinderical tube 31 and an outer cylindrical tube 33 in which the inner tube telescopes. The inflating apparatus is arranged so that the axes of the telescoping tubes extend vertically. The inner tube has an extension 31a of reduced diameter at the mouth thereof. The extension 31a is D-shaped in cross-section to be of a geometrically similar shape in cross-section as the ring 12, having an outside diameter slightly smaller than the inside diameter of the ring 12 so that the ring 12 would fit around the section 31a. To use the inflating apparatus, the glove package is placed over the mouth of the extension 31a as shown in phantom lines in FIG. 5 with the linear segment 12b of the ring adjacent to the linear portion of the extension 31a. The cuff portion 24a, which laps over the ring 12 and extends radially back toward the axis thereof, rests upon the flat planar circular surface provided on the end of the extension 31a of the mouth thereof. The skirt 15a, the liner 15, and the palm and finger portion of the glove 24 hang down inside of the inner tube 31. After the glove has been placed on the cuff of the inflating apparatus, the glove is inflated and the glove is donned in the same manner as described in U.S. Pat. No. 4,002,267.

The above described package makes it possible for persons desiring to put on the sterile gloves to very quickly and easily orient the glove package to the proper position and don the gloves without danger of contamination and without the need for the assistance of a second person. The above description is of a preferred embodiment of the invention and many modifications may be made thereto without departing from the spirit and scope of the invention which is defined in the appended claims.

We claim:

1. In an elastomeric glove package comprising a packaging ring and an elastomeric glove having the cuff portion stretched around the outside of said ring, the improvement wherein said ring is D-shaped having a linear segment and an arcuate segment and wherein said glove is oriented with respect to said ring so that the palm portion of said glove faces in a direction toward a plane containing said linear segment and parallel to the axis of said ring.

2. An elastomeric glove package as recited in claim 1, wherein said cuff portion passes through said ring and is stretched around said ring with the outside surface of said cuff portion engaging said ring.

3. An elastomeric glove package as recited in claim 2, wherein the cuff portion of said glove extends around both axial ends of said ring and radially back toward the axis of said ring and the edge of the cuff portion defines an opening at the center of said ring, the finger and palm portion of said glove passing through said opening.

4. An elastomeric glove package as recited in claim 2, wherein a flexible liner passes through said ring surrounding the palm and finger portion of the glove and extends around the ring to the outside thereof between the cuff portion of said glove and said ring.

5. An elastomeric glove package as recited in claim 1, wherein the arcuate segment of said ring has an inner diameter of at least 4¼ inches and has an outside diameter no greater than 5¼ inches.

6. An elastomeric glove package as recited in claim 4, wherein the inner diameter of the arcuate segment of said ring is about 4¾ inches and the outer diameter of the arcuate segment of said ring is about 4 9/16 inches.

7. An elastomeric glove package as recited in claim 1, wherein said linear segment subtends an angle of about 100°, the vertex of said angle being at the axis of said arcuate segment.

8. An elastomer glove package as recited in claim 1, wherein said linear segment subtends an angle in the range of from 45° to 180°, the vertex of said angle being at the axis of said arcuate segment.

9. An elastomeric glove package as recited in claim 8, wherein the angle subtended by said linear segment is about 100°.

10. An elastomeric glove package as recited in claim 1, wherein the thumb portion of said glove is positioned to be closest to a junction between said linear segment of said ring and said arcuate segment.

* * * * *